United States Patent [19]

Fahlvik et al.

[11] 4,239,730

[45] * Dec. 16, 1980

[54] AUTOCLAVE APPARATUS FOR STERILIZING OBJECTS

[75] Inventors: Hans A. Fahlvik, Sloinge; Kurt E. Sandquist, Getinge, both of Sweden

[73] Assignee: Aktiebolaget Electrolux, Stockholm, Sweden

[ * ] Notice: The portion of the term of this patent subsequent to Nov. 28, 1997, has been disclaimed.

[21] Appl. No.: 929,734

[22] Filed: Jul. 31, 1978

Related U.S. Application Data

[63] Continuation of Ser. No. 762,346, Jan. 25, 1977, abandoned.

[30] Foreign Application Priority Data

Jan. 26, 1976 [SE] Sweden ................................ 7600739

[51] Int. Cl.³ ............................ A61L 2/06; A61L 2/24
[52] U.S. Cl. .................................... 422/109; 422/295; 422/112; 422/111
[58] Field of Search ........................ 422/26, 109-112, 422/114, 295

[56] References Cited

U.S. PATENT DOCUMENTS

| | | | |
|---|---|---|---|
| 3,086,837 | 4/1963 | Wilkinson et al. | 91/94 |
| 3,093,449 | 6/1963 | Kotarski et al. | 21/56 |
| 3,450,487 | 6/1969 | Wallden | 21/96 |
| 3,481,688 | 12/1969 | Craig et al. | 21/94 |
| 3,531,300 | 9/1970 | Greenberg et al. | 21/94 |
| 3,910,761 | 10/1975 | Hopkins | 21/94 |
| 4,003,703 | 1/1977 | Montgomery et al. | 21/56 |
| 4,127,384 | 11/1978 | Fahlvik et al. | 422/295 |

FOREIGN PATENT DOCUMENTS 2363468 7/1975 Fed. Rep. of Germany ............. 21/94

*Primary Examiner*—Bradley R. Gerris
*Attorney, Agent, or Firm*—Alfred E. Miller

[57] ABSTRACT

An autoclave for treating products, such as sterilizing cans and ampoules, the apparatus having a chamber into which a supply conduit is connected provided with a medium, such as steam, and a further supply conduit provided with at least one control medium, for example compressed air. The apparatus is also provided with a discharge conduit and a vent conduit. The apparatus and method achieves the intended sterilization of the products by operating the system as near as possible to the temperature tolerance of the plastic packaging of the products being treated.

4 Claims, 2 Drawing Figures

AUTOCLAVE APPARATUS FOR STERILIZING OBJECTS

This is a continuation of application Ser. No. 762,346, filed Jan. 25, 1977, now abandoned.

BACKGROUND OF THE INVENTION

Autoclaves are known in which a main medium can be defined as a medium by which the intended main function is achieved, and the control medium is defined as having an auxiliary function by which the main function is obtained. In sterilization by heat and moisture the main medium is steam. In sterilization by gas the main medium can be formalin, and in hot air sterilizers it is hot air. In sterilization by gas, the control medium is a heat conveying medium, for example steam.

As stated above, autoclaves of this type are known, but they have drawbacks and are therefore considered unsatisfactory. For example, when the items in the chamber before sterilization are heated for a period of time towards the sterilization temperature, a pressure increase occurs in the packaging, or a temperature increase is caused in the chamber, which may entail impairment of the contents, or its packaging.

A main object of the present invention is to treat such goods in the autoclave which are subject to sterilization at a temperature that is as high as possible, but yet below a temperature at which the packaging material is damaged. One example of such goods are pharmaceutical products encased in plastic ampoules such as polypropylene, which at a comparatively low temperature the softening compounds in the plastic material starts to diffuse out of the material. Moreover, in the hottest part of a packaging which is not in contact with the liquid in the packaging, the plastic will commence shrinking. Furthermore, the packaging is deformed and cracks may appear therein. This situation cannot be tolerated because of the risk of bacteria growing into the aforesaid cracks.

It is desired to work as near as possible to the temperature tolerance of the plastic without exceeding or reaching this temperature, in order to achieve the required sterilization of the products. The material of the packaging can easily be deformed at a high temperature and this material does not tolerate great differences in pressure between the ambient and the contents. Therefore, the exterior pressure must all the time be balanced against the interior pressure of the package. In this connection, it is known to apply a support pressure, for example by using compressed air, for such balancing purposes.

It has been proposed initially to supply only steam for heating in order to achieve the quickest possible heating of the autoclave chamber. The autoclave has a steam supply conduit with a control valve which is dependent on a thermostat whose sensing body is placed in the supply conduit after the valve. The thermostat is then set at a temperature which is above the intended sterilization temperature in the chamber. The vent conduit has a control valve which is dependent upon a pressostat that reacts according to the pressure in the chamber. The pressostat is set so as to maintain a steam pressure corresponding to the sterilization temperature. Therefore, assuming that the sterilization temperature is 108° C., the steam pressure will be 0.4 at. The supply of steam continues also after the intended pressure has been obtained, but simultaneously steam is permitted to flow out through the vent conduit. At the same time, a thermostat, whose sensing body is located in a package or in a test bottle, controls the temperature in the packages. When the temperature has reached a given value, for instance 70° C., the pressure in the packaging commences to rise above the pressure of the chamber. To prevent this interior pressure from deforming the packaging, a support pressure, for example generated by some gas, can be used in the chamber. The most suitable gas with respect to temperature and pressure would be helium or hydrogen, which easily mix with steam. For practical reasons, however, air is used. If it is desired to increase the pressure in the chamber by means of compressed air it has been found that there will not be a uniform momentous distribution of air in the entire chamber, but a series of pockets formed with steam surrounded by air. Instead of obtaining only a partial pressure, the steam pockets will be compressed to the same pressure as the total pressure. Thus, a pressure increasing to a value corresponding to the total pressure, which is about 0.9 at. is obtained in a gas bubble. The temperature of the steam increases from 108° to 118° C.

In order to solve the aforesaid problem it is hereby proposed to blow the steam out of the chamber, instead of supplying a support pressure. The steam is then replaced by a homogeneous mixture of steam and air, which components are mixed in the supply conduit before being introduced into the chamber. In this way, it is possible to achieve a considerable improvement of the conditions in the chamber. However, experience has shown that also by this procedure too high a temperature may occur in the chamber. This is avoided by the teachings of the present invention by means of a short injection of cooling water and the exchange of the main medium for the control medium.

The invention will be described hereinafter with reference to an autoclave shown diagrammatically in the drawings.

FIG. 1 is a diagram of an autoclave with valves constructed according to the teachings of the present invention, and, FIG. 2 is the same diagram as FIG. 1, but on a reduced scale, and with the addition of a control system for the valves.

DESCRIPTION OF THE PREFERRED EMBODIMENT

Figure 1:
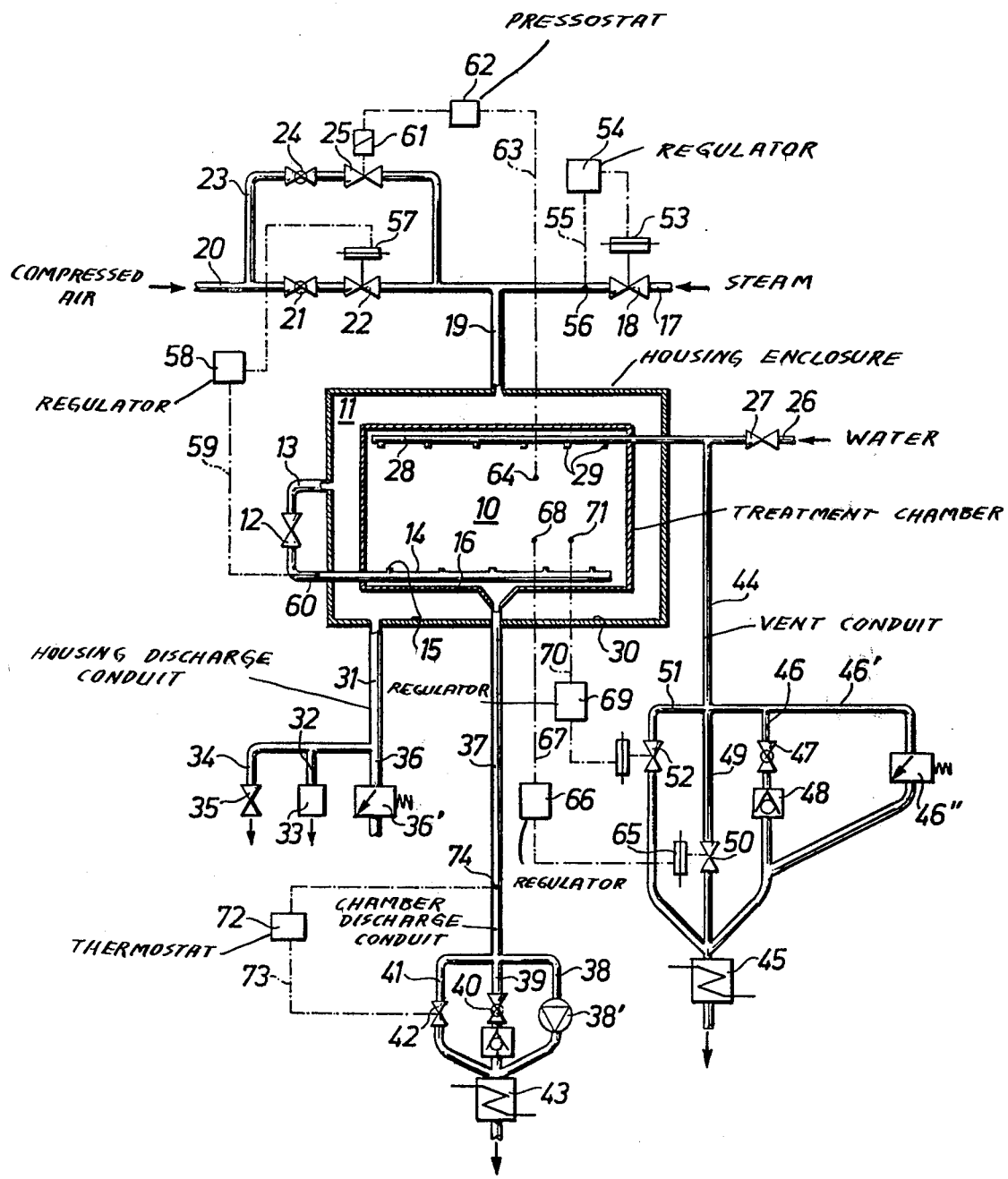

The autoclave shown in FIG. 1 has a treatment chamber 10 shrouded by a housing 11 which communicates with the chamber by means of a conduit 32 having a valve 12. The connecting conduit 13 extends generally from the upper part of the housing 11 and opens into the chamber 10 by means of tubes 14 provided with distributing nozzles 15 located at the bottom 16 of the chamber 10.

A conduit 17 with a shut-off valve (not shown) is adapted to conduct steam through a valve 18 into a mixing chamber 19 that communicates directly with the housing 11. A compressed air conduit 20 provided with a shut-off valve (not shown) is connected to the mixing chamber 19 by means of a throttle 21 and a valve 22. The arrangement also has a bypass conduit 23 around the valve 22 which is provided with a throttle 24 and a valve 25.

FIG. 1 also shows a water pipe 26 with a shut-off valve (not shown) and a valve 27, the pipe 26 opening into the upper part of the chamber 10 by means of tubes 28 with distributing nozzles 29.

The present autoclave also has a system by which the working media are let or drawn out. This system comprises a discharge conduit 31 at the bottom 30 of the housing 11 having a branch 32 with a steam trap 33 and a condensate water drain and another parallel branch 34 includes a valve 35. A further branch 36 is shown having a relief valve 36'.

As further seen in FIG. 1, a discharge conduit 37 is connected to the bottom 16 of the chamber 10. The conduit 37 has a branch 38 having a vacuum pump 38' and a branch 39 with a throttle valve 40, as well as a branch 41 having a drain valve 42. All these branches pass through a condenser 43 to an outlet drain. The valve 42 is preferably a piston valve controlled by a thermostat 72 positioned in an impulse conduit 73 communicating with a temperature sensing body 74 in the conduit 37.

The upper part of the chamber 10 has an outlet through which the tubes 28 pass. Part of the pipe 26 and a conduit 44 connected thereto are provided with branches passing through a condenser 45. The outlet conduit 44 from the chamber has a branch 46 with a throttle 47 and a non-return valve 48, a branch 49 with a valve 50, and a branch 51 with a valve 52. In addition, a branch 46' is provided with a relief valve 46".

It should be mentioned that the autoclave has also various known details which are not shown in FIG. 1, for example, safety valves, filters, means for operating the door and sealing means for the door, several measuring devices and, if desired, water tanks for specially treated water for special conditions.

Up to this point the autoclave has been specified in principle without describing the control devices, i.e. for operating the valves.

Figure 2:
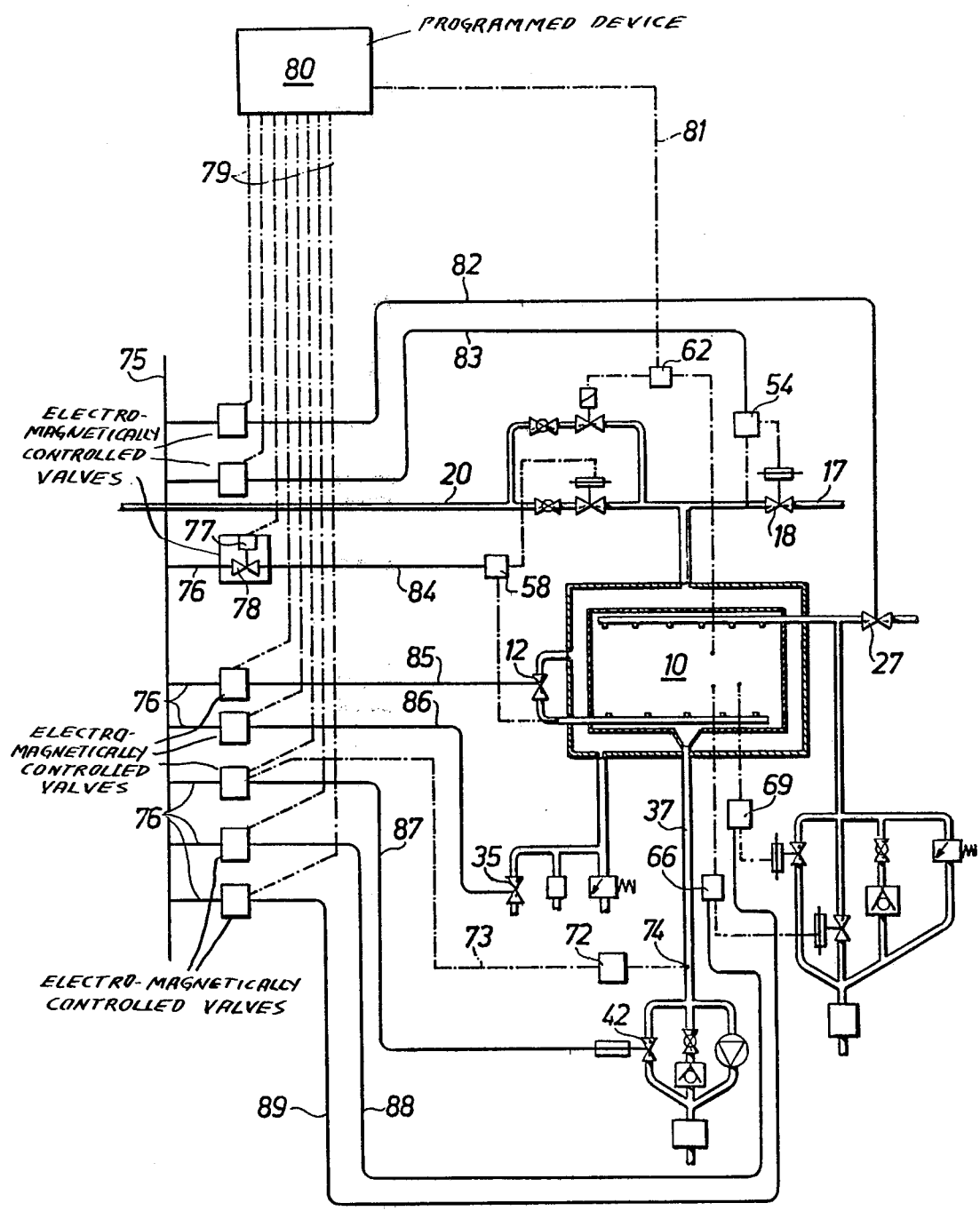

Referring now to FIG. 2, the control system of the autoclave comprises a supply of compressed air by several electromagnetically controlled valves in conduits to operating devices of the above valves in the conduits for the working media in the autoclave. The electromagnetic valves are operated by a control panel (not shown) together with programmed devices, time control devices, etc.

As seen in FIG. 1, the operating device 53 of the valve 18 in the steam conduit 17 receives compressed air by a temperature-controlled regulator 54, which receives impulses by a conduit 55 from a sensing body 56 positioned in the conduit 17 in the downstream side after the valve 18.

The valve 22 in the air conduit 20 has an operating device 57 which receives impulses from a temperature controlled regulator 58 connected to an impulse conduit 59 having a sensing body 60 situated in the connecting conduit 13 between the housing 11 and the chamber 10 immediately ahead of the inlet to the chamber through the tubes 14.

The valve 25 in the second air conduit 23 has an operating device 61 controlled by a pressostat 62 with an impulse conduit 63 connected to a point 64 in the chamber 10. Preferably, the valve 25 is a magnet valve controlled directly by the pressostat.

A valve 50 in the discharge part in the conduit 49 is controlled by a pressure controlled regulator 66 receiving pressure impulses through a conduit 67 from a sensing body 68 in the chamber 10. The valve 52 in the conduit 51 is controlled by a pressure controlled regulator 69, which by means of a conduit 70 senses the pressure at a point 71 in the chamber 10.

In order to activate the above described regulators 54, 58, 66 and 69, the pressostat 62, and the valves 12, 27, 35 and 42, the apparatus uses a control system which is diagrammatically shown in FIG. 2. It includes a compressed air supply conduit 75 with a multiplicity of branches 76 to valves 78 controlled by electromagnets 77. For the sake of simplicity, only one valve 78 is shown in detail, the others being identical. The electromagnets 77 are connected by conduits 79 to a programmed device 80 which comprises known components, such as time-controlled devices and devices controlled by the condition existing in the autoclave chamber 10. The programmed device can have means to perform different programs, for example, sterilization at 110° C. or at 120° C. When the programmed device 80, by means of a conduit 79, sends an impulse to a valve 78, compressed air is admitted by one or several of the conduits 82-89 to the respective operating device in the conduits for working media to the autoclave. The pressostat 62 is activated directly from the programmed device 80 by electric impulses sent through a conduit 81 and is furthermore controlled by the pressure in the chamber.

As previously stated hereinabove, the drain valve 42 is controlled by the thermostat 72, whose impulse conduit 73 connects to an electromagnet 77 of an air valve in the conduit 87 to the operating device of the valve 42.

In a practical embodiment, regulators of Minneapolis-Honeywell Regulator Company Type PP 97 A for pressure control and Type LP 97 A for temperature control have been used in the present apparatus.

The above-described arrangement operates in the following manner:

When the items have been placed in the chamber 10 and the autoclave door has been closed, the valve 18 in the steam conduit 17 is opened so that steam is suppled to the chamber by means of the mixing chamber 19, the housing 11 and the connection conduit 13. In addition to the items to be treated, there is also air in the chamber, and this air is caused to be expelled through the discharge conduit 37. The valve 52 in vent conduit 44 does not open until the pressure in the chamber has reached a set value. Air and condenstate are passed through the valve 42 until the temperature of the mixture has reached a given value and the valve 42 closes and the condenstate is thereafter expelled through the valve 40. The temperature at which the valve 42 closes is adjustable by means of the thermostat 72. In the beginning the air in the chamber is expelled and then steam condenses on the chamber wall and on the items in the chamber, during which process heat is given off. The temperature in the chamber increases rapidly, and during this heating cycle only steam is supplied. The temperature in the chamber is regulated by pressure controlled devices, i.e. the regulator 69. Therefore, the items are heated and when a given temperature is reached, the pressure in the items exceeds the saturation pressure of the surrounding steam and in order to avoid deformation of the packages one has previously tried to apply a support pressure by supplying a second medium, for example, compressed air. The magnitude of this support pressure is related to the end temperature of the items, which in this case is the same as the sterilization temperature. However, if the full support pressure should be applied directly after the preceding steam phase in the chamber, the steam therein would be compressed and this compression would result in a considerable increase in temperature within the chamber which is unacceptable with respect to the quality of the items being treated. Therefore, special measures have to be taken, and in accordance with the teachings of the present invention, the working media in the chamber are exchanged occasionally. This exchange can be initiated by a temperature sensor housed in a plastic ampoule in the chamber. When the temperature in the latter has risen to a value between 70° C. and 90° C. the pressure in the ampoule has reached the same magnitude as in the ambient. Four typical examples of exchange of working media in the present autoclave are set forth hereinbelow:

(1) The valve 52 in the discharge outlet conduit is closed and instead the other valve 50 is opened. The regulators 69 and 66 of the two valves are adjusted to different total pressure in the chamber. At the same time, the pressostat 62 is activated so that the valve 25 in the air conduit is opened and compressed air is supplied to the chamber 10. Thus, the steam in the chamber is expelled and there is an occasional exchange of working media. This occurs in so short a time that the temperature of the items is not affected to any great extent and after this short transitional phase, the proper sterilization process can be initiated.

(2) One proceeds generally as in example 1 but the pressostat 62 is activated a short time before the discharge valves 52 and 50 are shifted. Because the regulator 69 is adjusted to a lower pressure than the regulator 66, the steam is expelled quicker, but in other respects, the procedure is the same.

(3) The valve 52 in the discharge conduit is closed and the valve 50 is opened simultaneously as the pressostat 62 is activated so that air supply begins. At the same time, the valve 27 is opened so that a smaller quantity of water is injected through the tubes 28 with the nozzles 29 in the top wall of the chamber. Thus, a rapid condensation of the steam in the chamber occurs at the same time as the pressure therein is maintained by the aid of the compressed air. The condensate exits through the conduit 37.

(4) The same procedures as in example 3 are followed, but furthermore the valve 18 in the steam conduit and the valve 22 in one branch of the compressed air conduit are activated.

In the examples 1 and 2 it takes some time before the exchange of media has taken place and a certain temperature decrease of the items cannot be avoided. On the other hand, in the examples 3 and 4, the exchange occurs so rapidly that the temperature decrease of the items will scarcely be noticed.

After the transitional phase of media exchange, the sterilization process is started, as mentioned above. During this process the valve 50 is active and steam and compressed air are supplied through the valves 18, 22 and 25. This process can be performed in known manner.

The invention is not limited to the apparatus shown and described and to the method described in connection therewith. Thus, the invention can be modified in many respects within the scope defined by the following claims. It should particularly be observed that the description deals with an especially favorable embodiment of the autoclave with a chamber for the items which is surrounded by a housing. However, according to the principles of the invention, in such an autoclave the working media can also be conducted past the housing and directly into the chamber. Furthermore, it is also possible to apply the invention to an autoclave without a housing.

What is claimed:

1. In an autoclave for sterilizing objects comprising a treatment chamber, a supply conduit for steam, a supply conduit for compressed air, a discharge conduit, and a vent conduit, said autoclave being provided with a control system having a plurality of adjusting controlling valves, each of said adjusting controlling valves being operative with a respective steam supply conduit, compressed air supply conduit, discharge conduit and vent conduit whereby said steam supply conduit is opened for heating of said chamber with the objects therein to sterilizing temperatures, whereupon before the sterilizing period occurs a first valve in the vent conduit and a second valve in the compressed air conduit are opened so that initially only the steam is supplied to said chamber until a given condition has been reached therein, said steam being thereafter replaced by means of a mixture of said steam and said compressed air.

2. An arrangement as set forth in claim 1 further comprising a top interior wall in said chamber and a plurality of spray nozzles mounted adjacent to said top interior wall of said chamber, and a conduit having a valve being provided for supply of water to said autoclave, said control system being arranged during the exchange of steam for a mixture of steam and compressed air to open said valve in said water conduit for supply of a small quantity of water to said spray nozzle adjacent to said top interior wall of said chamber.

3. An autoclave as claimed in claim 1 further comprising a conduit having spaced nozzles being located in the bottom of said chamber for supplying steam and air to said chamber.

4. An autoclave as claimed in claim 1 wherein said steam and compressed air supply conduits, discharge conduit and vent conduit and the control system have combined means for ensuring a continuous flow of air and/or steam through said chamber during sterilization depending on the pressure and temperature therein.

* * * * *